United States Patent
Haag et al.

(10) Patent No.: US 6,946,462 B2
(45) Date of Patent: Sep. 20, 2005

(54) N-MONOACYLATED DERIVATIVES OF O-PHENYLENEDIAMINES, THEIR ANALOGS AND THEIR USE AS PHARMACEUTICAL AGENTS

(75) Inventors: Rainer Haag, Heiligenhafen (DE); Ulrike Leser-Reiff, Penzberg (DE); Anja Limberg, Munich (DE); Michael Weidner, Penzberg (DE); Gerd Zimmermann, Linkenheim (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/823,211

(22) Filed: Apr. 13, 2004

(65) Prior Publication Data

US 2004/0192744 A1 Sep. 30, 2004

Related U.S. Application Data

(63) Continuation of application No. 10/212,901, filed on Aug. 6, 2002, now Pat. No. 6,869,953.

(30) Foreign Application Priority Data

Aug. 7, 2001 (EP) ............................................. 01118741

(51) Int. Cl.$^7$ ..................... C07D 237/02; C07C 43/02; A61K 31/501; A61K 31/4439; A61P 35/00

(52) U.S. Cl. ..................... 514/247; 514/317; 514/365; 514/367; 514/374; 514/385; 514/411; 514/415; 514/443; 514/464; 544/239; 548/427; 548/452; 549/49; 549/70; 549/462; 549/483; 564/218; 564/308

(58) Field of Search ..................... 544/239; 546/192; 548/427, 452; 549/49, 70, 462, 483; 564/218, 308; 514/247, 317, 365, 367, 374, 385, 411, 415, 443, 464

(56) References Cited

U.S. PATENT DOCUMENTS 3,810,910 A * 5/1974 Friedrich et al. ........ 548/304.7
4,001,416 A    1/1977 Pommer et al.

FOREIGN PATENT DOCUMENTS

| DE | 2 062 265 | 5/1972 |
|----|-----------|--------|
| EP | 242 851 | 10/1987 |
| EP | 847 992 | 6/1998 |
| FR | 2 150 961 | 4/1973 |
| FR | 2 167 954 | 8/1973 |
| FR | 2 193 548 | 2/1974 |
| GB | 2 165 537 | 4/1980 |
| WO | WO 01/38322 | 5/2001 |
| WO | WO 01 68604 | 9/2001 |
| WO | WO 01 72705 | 10/2001 |

OTHER PUBLICATIONS

Cecil Textbook of Medicine, edited by Bennet, J.C., and Plum F., 20th edition, vol. 1, 1004–1010, 1996.*
Wolft Manfred E. "Burger's Medicinal Chemistry, 5ed, Part 1", John Wiley & Sons, 1995, pp. 975–977.*
Banker, G.S. et al, "Modern Pharmaceutices, 3ed.", Marcel Dekker, New York. 1996, p. 596.*
Rastogi et al., Indian J. Chem., Sect. B, 21B (5), pp. 485–487 (1982).
Moll et al., Z. Chem. 4, 17, pp. 133–134 (1977); also Chem. Abstracts, 87:84749h (1977).
Hassan et al., Indian J. Chem., Sect. B: Org. Chem. Incl. Med. Chem. 39B(10), pp. 764–768 (2000).
Banihashemi et al., J. Appl. Polyn. Sci., 35, pp. 51–57 (1979).
Vyas et al., J. Indian Chem. Soc., 68(5), pp. 294–295 (1991).
Kabanos et al., J. Chem. Soc. Dalton Trans., pp. 2729–2733 (1992).
Adembri et al., J.Chem. Soc. Perkin I, 9, pp. 1022–1026 (1974).
Chimichi et al., J.Chem. Soc. Perkin II, 2, 9, pp. 1339–1343 (1980).
Prewysz–Kwinto, Chem Abstract XP002188608 & Khim. Geterotsikl. Soedin, (6), pp. 756–759 (1987).
Hatchard W.R., Chem Abstract XP002228920, J. Org. Chem., vol. 29, pp. 665–668 (1964).
Zarin, P.P., et al., Chem Abstract XP002228921, Chem. Heterocycl. Compd., vol. 10, pp. 96–98 (1974).
Gortinskaja, et al., Chem Abstract XP002228922, Zh. Obshch. Khim., vol. 25, pp. 2313–2315 (1955).
Balaban, King, Chem Abstract XP002228923, J. Chem. Soc., vol. 127, p. 2710 (1925).
HU 155 098 A, Chem Abstract XP002228924, Chinoin Gyogyszer Es Vegyeszeti Termekek Gyora Rt, (1966).

(Continued)

*Primary Examiner*—Venkataraman Balasubramanian
(74) *Attorney, Agent, or Firm*—George W. Johnston; Patricia S. Rocha-Tramaloni; Brian C. Remy

(57) ABSTRACT

New compounds represented by the formula

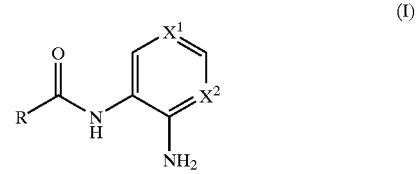

(I)

or pharmaceutically acceptable salts or prodrugs thereof, wherein
$X^1$ and $X^2$ are each independently selected from a CH group or a nitrogen atom; and
R is an optionally substituted five or six membered nonaromatic carbocyclic ring or a nonaromatic or aromatic heterocyclic ring, whereby the ring is optionally condensed with a 6-membered, optionally substituted carbocyclic aromatic ring.

9 Claims, No Drawings

OTHER PUBLICATIONS

Holan G., et al, Chem Abstract XP002228925, J. Chem. Soc. C., pp. 20–25 (1967).
De Selms R.C., Chem Abstract XP002228926, J. Org. Chem., vol. 27, pp. 2163–2165 (1962).
Prewysz–Kwinto A., Chem Abstract XP002228927, Chem Heterocycl. Compd., vol. 23, No. 6, pp. 624–627 (1987).
Bedair A.H., Chem Abstract XP002228928, J. Prakt. Chem., vol. 329, No. 2, pp. 359–364 (1987).
Hudkins R.L., Chem Abstract XP002228929, Heterocycles, vol. 41, No. 5, pp. 1045–1050 (1995).
Zalesov V.V., et al., Chem Abstract XP002228930, Russ. J. Org. Chem., vol. 31, No. 8, pp. 1104–1108 (1995).
Burgart Ya. V., et al., Chem Abstract XP002228931, Russ. J. Org. Chem., vol. 34, No. 3, pp. 375–380 (1998).
Salakhov M.S., et al., Chem Abstract XP002228932, Russ J. Org. Chem., vol. 35, No. 3, pp. 397–401 (1999).
Blood, Chem Abstract XP002228933, 42nd Annual Meeting of the American Society of Hematology; San Francisco, CA, vol. 96, No. 11 Part 2 (2000).
Nicolaus, B J R, Chem Abstract XP002197412, Decision Making in Drug Research, XX, XX, pp. 173–186 (1983).

* cited by examiner

N-MONOACYLATED DERIVATIVES OF O-PHENYLENEDIAMINES, THEIR ANALOGS AND THEIR USE AS PHARMACEUTICAL AGENTS

This application is a continuation of Ser. No. 10/212,901, filed Aug. 6, 2002, now U.S. Pat. No. 6,869,953.

FIELD OF THE INVENTION

This invention relates to antitumor agents and, in particular, to the use of monoacylated, aromatic, o-diamine substituted aromatic or heteroaromatic six membered ring systems or pharmaceutically-acceptable salts thereof. Based on their antiproliferative and differentiation-inducing activity, which results in inhibition of tumor cell proliferation, induction of apoptosis and inhibition of invasion, these compounds are useful for the treatment of diseases such as cancer in humans or animals.

BACKGROUND

Cancer is one of the major causes of death. Cancer exceeds heart and cerebrovascular diseases in causing death. Accordingly, many studies have been conducted with enormous expense and time to overcome cancer. However, despite a variety of therapies such as surgical operation, radiation therapy and chemotherapy, there is still a great need for improved anticancer therapeutics. Among these therapies, chemotherapy is one of the main areas for cancer treatment. Most drugs show their effect by inhibiting DNA from expressing their cytotoxicity and as a result, injuring tumor cells. However, chemotherapy lacks selectivity and consequently, does not sufficiently differentiate between tumor cells and normal cells, and therefore, adverse reactions expressed in normal cells have limited their use in therapy. Up to now, no satisfactory drugs are believed to have been discovered, and thus, an anticancer drug with reduced toxicity, better tolerability and a high therapeutic effect is very much desired.

Differentiation-inducing, antiproliferative agents among anticancer drugs are intended to induce differentiation of tumor cells for controlling their infinite proliferation and survival, rather than directly killing the cells. These agents are inferior to the anticancer drugs that directly kill tumor cells, during the formation of a tumor, but have reduced toxicity and different selectivity, and exert additive effects in combination with other antitumor therapeutics or treatments.

EP-A 0 847 992 describes monoacylated o-phenylendiamine derivatives as cell differentiation inducers. The same type of compounds is also the subject of EP-A 0 242 851. The compounds described in these applications are almost exclusively o-phenylene derivatives monoacylated with derivatives of benzoic acid. However, there is still a need to provide compounds with improved properties such as increased tolerability, less toxicity and less side effects.

Monoacylated o-phenylendiamines are known in the art as precursors for the preparation of the corresponding benzimidazoles, such preparation methods are described in DE-A 2 062 265; FR 2 167 954; Rastogi, R., and Sharma, S., Indian J. Chem., Sect. B, 21B (5) (1982) 485–487; Moll, R., et al., Z. Chem. 17 (1977) 133–134; and Hassan, H., et al., Indian J. Chem. 39B (2000) 764–768.

A preferred embodiment of this invention provides compounds which exhibit differentiation-inducing and antiproliferative effects and therefore are useful as pharmaceutical agents for treatment of malignant tumors, autoimmune diseases, dermatologic diseases and diseases caused by parasites.

This invention relates to new mono-N-acylated o-diamino substituted aromatic or heteroaromatic six membered ring systems and its pharmaceutically acceptable salt, which inhibit cell-proliferation activity and are therefore useful for the treatment of diseases such as cancer in humans or animals. This invention also relates to processes for the manufacturing of these o-diamine derivatives, to pharmaceutical compositions containing them and to their use in the manufacture of drugs for the treatment of diseases like cancer.

SUMMARY OF THE INVENTION

In an embodiment, the present invention is directed to a compound of formula

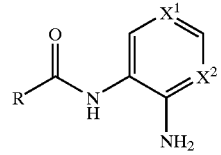

(I)

or a pharmaceutically acceptable salt or prodrug thereof, wherein
$X^1$ and $X^2$ are each independently selected from a CH group or a nitrogen atom; and
R is an optionally substituted five or six membered nonaromatic carbocyclic ring or a nonaromatic or aromatic heterocyclic ring, whereby the ring is optionally condensed with a 6-membered, optionally substituted carbocyclic aromatic ring,
provided that if $X^1$ and $X^2$ are both CH, R is not a halogenated benzothiophene; halogenated thiazolyl; N-benzyl-2-acetylamino-4,5-dimethylpyrrole-3-yl; optionally substituted 1,4-oxathiine-3-yl; optionally substituted pyridinyl; or pyridazine-5-yl which is substituted by one to three substituents selected from methyl, methoxy, methoxycarbonyl or carboxyl;
and provided further that if one of $X^1$ or $X^2$ is a nitrogen atom and the other is a CH group, or $X^1$ and $X^2$ are both nitrogen atoms, then R is not an optionally substituted pyridinyl.

In another embodiment, this invention is directed to a pharmaceutical composition comprising, as an active ingredient, one or more compounds represented by the formula

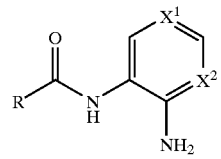

(I)

or a pharmaceutically acceptable salt or prodrug thereof, wherein
$X^1$ and $X^2$ are each independently selected from a CH group or a nitrogen atom; and
R is an optionally substituted five or six membered nonaromatic carbocyclic ring or a nonaromatic or aromatic heterocyclic ring, whereby the ring is optionally condensed with a 6-membered, optionally substituted carbocyclic aromatic ring; provided that R is not a substituted pyridinyl.

Yet another embodiment of this invention is directed to a method of treating cancer comprising administering to a patient in need of such treatment an effective amount of at least one compound of formula I.

A further embodiment of this invention is directed to a method of inhibiting tumor cell proliferation by inducing histone acetylation in a tumor cell due to adminstering to the tumor cell an effective amount of at least one compound of formula I.

DETAILED DESCRIPTION OF THE INVENTION

In an embodiment, the present invention is directed to a compound of formula

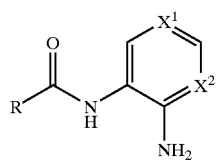

(I)

or a pharmaceutically acceptable salt or prodrug thereof, wherein $X^1$ and $X^2$ are each independently selected from a CH group or a nitrogen atom; and R is an optionally substituted five or six membered nonaromatic carbocyclic ring or a nonaromatic or aromatic heterocyclic ring, whereby the ring is optionally condensed with a 6-membered, optionally substituted carbocyclic aromatic ring, provided that if $X^1$ and $X^2$ are both CH, R is not a halogenated benzothiophene; halogenated thiazolyl; N-benzyl-2-acetylamino-4,5-dimethylpyrrole-3-yl; optionally substituted 1,4-oxathiine-3-yl; optionally substituted pyridinyl; or pyridazine-5-yl which is substituted by one to three substituents selected from methyl, methoxy, methoxycarbonyl or carboxyl;

and provided further that if one of $X^1$ or $X^2$ is a nitrogen atom and the other is a CH group, or $X^1$ and $X^2$ are both nitrogen atoms, then R is not an optionally substituted pyridinyl.

The $X^1$ and $X^2$ containing ring systems are phenyl, pyridine or pyrimidine whereby the phenyl ring may be substituted by one or two halogen atoms, preferably by chlorine.

The non-aromatic carbocyclic ring represented by R in the general formula (I) is understood as a carbocyclic ring that is constructed from single and double bonds to form a five or six membered ring. The ring contains at least one single sp3 hybridized carbon atom. Examples include cyclopentane, cyclohexane, cyclohexene, cyclohexadiene, and the preferred is cyclohexene. The nonaromatic or aromatic heterocyclic ring R in formula (I) may be a five or six membered, saturated or unsaturated ring containing 1 to 4 heteroatoms selected from nitrogen, oxygen or sulfur. This heterocyclic ring includes, for example, piperazine, piperidine, morpholine, pyrrolidine, pyrimidine, pyrazine, pyridazine, tetrahydro-pyridazine, pyrrole, furane, imidazole, pyrazole, dihydro-pyrazole, triazole, thiophene, thiazole, oxazole, isothiazole, isoxazole, dihydro-isoxazole, thiadiazole, tetrazole whereby the heterocyclic rings pyrrolidine, dihydropyrazole and tetrahydro-pyridazine may carry an oxo-group. Preferred rings are thiophene, furane, pyrazole, imidazole, isothiazole, isoxazole and triazole.

The above mentioned heterocycles may be fused with a 6 membered, optionally substituted carbocyclic aromatic ring, such as benzothiophene, benzofurane, indole, benzimidazole, indazole, benzothiazole, benzoxazole, quinoline, isoquinoline and benzoindole; and preferably benzofurane, benzothiophene and indole.

The ring R or its condensed derivatives may be substituted with one or more substituents selected from aralkyl, aryl, hetaryl, hetaralkyl, $C_1$–$C_6$ alkyl, $C_2$–$C_6$ alkenyl, $C_2$–$C_6$ alkinyl, $C_1$–$C_7$ acyl, $C_1$–$C_6$ alkyloxy, $C_2$–$C_6$ alkenyloxy, $C_1$–$C_6$ alkylamino, di($C1$–$C_6$)alkylamino, amino, hydroxy, halogen, nitro, carboxyl, carboxamido, aminocarbonyl or trifluoromethyl groups.

Aryl, hetaryl, aralkyl and hetaralkyl substituents which may be substituents of the ring R in the general formula (I) may itself be substituted by one or more substituents selected from $C_1$–$C_6$ alkyl, $C_2$–$C_6$ alkenyl, $C_2$–$C_6$ alkinyl, $C_1$–$C_7$ acyl, $C_1$–$C_6$ alkyloxy, $C_1$–$C_6$ alkylamino, $C_1$–$C_6$ dialkylamino, amino hydroxy, halogen, nitro, carboxyl, carboxamido, aminocarbonyl, trifluoromethyl groups.

An aryl group represents a carbocyclic conjugated ring system, for example phenyl, naphthyl, preferably phenyl, which may be unsubstituted or substituted with the above-mentioned substituents.

An aralkyl group denotes the combination of an aryl group described above with a $C_1$–$C_6$ alkyl group connected through the alkyl part. Examples are benzyl, phenethyl and naphthylmethyl, preferred is benzyl and phenethyl wherein the phenyl ring may be substituted by the above-mentioned substituents.

Hetaryl groups which may be substituents of the ring R represent a mono- or bicyclic conjugated ring containing 1 to 4 heteroatoms selected from nitrogen, oxygen or sulfur and carbon atoms to fully saturate the ring. Such rings include, for example, piperazine, piperidine, morpholine, pyrrolidine, pyridine, pyrimidine, pyrazine, pyridazine, pyrrol, furane, imidazole, pyrazole, triazole, thiophene, thiazole, isothiazole, isoxazole, thiadiazole, tetrazole and oxazole, and preferred are thiophene, furane, pyrazole, imidazole, isothiazole, isoxazole, triazole pyridine, pyrimidine, pyrazine, benzofurane, indole, benzothiophene and quinoline.

A hetaralkyl group means the combination of a hetaryl group described above with a $C_1$–$C_6$ alkyl group connected through the alkyl part to the residue, preferred are pyridylmethyl, thienylmethyl and imidazolylmethyl.

$C_1$–$C_6$ alkyl residues as such or in combinations with other residues mean preferably methyl, ethyl, propyl, isopropyl or tert-butyl.

$C_2$–$C_6$ alkenyl means preferably allyl or pentadienyl. $C_2$–$C_6$ alkinyl means preferably propargyl.

$C_2$–$C_6$ alkenyloxy means preferably allyloxy.

$C_1$–$C_7$ acyl means —C(O)—$C_1$–$C_6$-alkyl or —C(O)H, preferably an acetyl group.

The alkyl residues can optionally be interrupted once or several times by heteroatoms (O, S, N) to form, for example, $CH_3$—O—$CH_2$—$CH_2$—O residue.

Halogen is understood as fluorine, chlorine, bromine, iodine, preferably fluorine or chlorine.

Preferred compounds are compounds of formula I wherein $X^1$ and $X^2$ are CH.

A further embodiment of the invention is a pharmaceutical composition containing as an active ingredient a compound of formula I

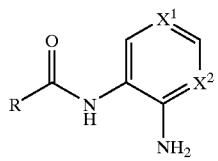

(I)

or a pharmaceutically acceptable salt or prodrug thereof, wherein $X^1$ and $X^2$ are each independently selected from a CH group or a nitrogen atom; and R is an optionally substituted five or six membered nonaromatic carbocyclic ring or an nonaromatic or aromatic heterocyclic ring, whereby the ring is optionally condensed with a 6-membered, optionally substituted carbocyclic aromatic ring; provided that R is not an optionally substituted pyridinyl.

Preferred pharmaceutical compositions are compositions containing a compound of formula I wherein X is CH and R is an unsubstituted or substituted benzofurane, benzothiophene, indole cyclohexene, pyrazole, thiazole, pyrrole, isoxazole or furane ring.

In a preferred embodiment, the active ingredients are benzofuran-2-carboxylic acid (2-amino-phenyl)-amide; 5,6-Dimethoxy-benzo[b]thiophene-2-carboxylic acid (2-amino-phenyl)-amide; 5-Propoxy-1H-indole-2-carboxylic acid (2-amino-phenyl)-amide; 5-Allyloxy-1H-indole-2-carboxylic acid (2-amino-phenyl)-amide; 7-Methoxy-benzofuran-2-carboxylic acid (2-amino-phenyl)-amide; 7-Methoxy-benzo[b]thiophene-2-carboxylic acid (2-amino-phenyl)-amide; and Thiazole-4-carboxylic acid (2-amino-phenyl)-amide.

Another embodiment of the invention is directed to a method for treating cancer by administering to a patient in need of such treatment an effective amount of at least one compound of the formula

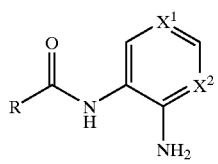

(I)

or a pharmaceutically acceptable salt or prodrug thereof, wherein $X^1$ and $X^2$ are each independently selected from a CH group or a nitrogen atom; and R is an optionally substituted five or six membered nonaromatic carbocyclic ring or an nonaromatic or aromatic heterocyclic ring, whereby the ring is optionally condensed with a 6-membered, optionally substituted carbocyclic aromatic ring.

The compounds of the general formula (I) is prepared according to well known processes. A carboxylic acid with the general formula (II) in which the residues R has the meaning described above is reacted with a compound with the general formula (III) in which the residue Y is a nitro-, amino- or a protected amino group, and X is a carbon or nitrogen, and if X is a carbon, then the six membered ring may be substituted by at least one halogen atoms.

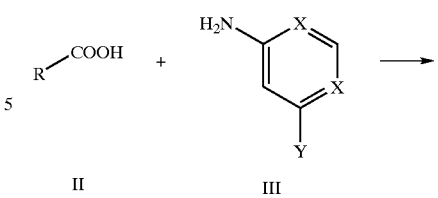

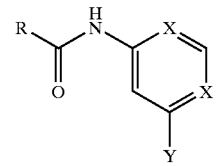

To accomplish this amide bond formation, the carboxylic acid is activated using methods known from peptide chemistry. Such activation reagents comprise the formation of mixed anhydrides using chloroformates, activation with carbodiimides, N,N'-carbonyldiimidazol, uroniumsalts, for example, O-(1H-benzotriazol-1-yl)-N,N,N',N'-tetramethyluronium tetrafluoro-borate, phosphorus based reagents e.g. bis-(2-oxo-3-oxazolidinyl)-phosphinic acid chloride. Carboxylic acids may also be converted to their acid chlorides using known methods, such as, by treatment with thionylchloride or oxalic acid dichloride. Y is an amino group and this second amino group may be protected to avoid bis-condensation of the carboxylic acid. The protection groups are cleaved after the formation of the amide bond. Protection groups for the amino group are known from peptide chemistry, for example, benzyloxycarbonyl (cleavage by hydrogenation or hydrobromic acid in acetic acid), t-butoxycarbonyl (cleavage by strong acids, such as, trifluoroacetic acid), 9-fluorenmethoxycarbonyl (cleavage by secondary amines, such as, piperidine). The nitro group can also be used as a precursor for the amino group. In this case, it is best to use a strongly activated carboxylic acid for the acylation of the weakly basic amino group, preferably the acid chloride. The amino group is generated through reduction of the nitro group either by catalytic hydrogenation, for example, over palladium on carbon or by treatment with reducing agents, for example, zinc in acetic acid, tin(II)chloride or sodium dithionite/$NaHCO_3$. It is also possible not to use a protecting group. In this case it is best to use an excess of acid to achieve a complete acylation of the primary amino groups. During work-up the desired product must be separated from the product resulting from the disubstitution. This is easily accomplished by exploiting the basic properties of the product using an ion exchanger, preferably a macroporous type ion exchanger, which can also be used in organic solvents.

The carboxylic acids and the aromatic amines are commercially available, described in the literature or can be prepared analogously to published methods.

Compounds of the general formula I can contain one or several chiral centers and can then be present in a racemic or in an optically active form. The racemates can be separated according to known methods into the enantiomers. Preferably, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The compounds of the present invention may exist as salts of organic or inorganic acids. Salts such as acetates, citrates or hydrochlorides are mainly used as pharmaceutically acceptable materials which are produced in the usual manner, for example, by titrating the compounds with or organic or inorganic acids selected from acetic acid, citric acid or hydrochloric acid.

The salts are usually purified by reprecipitation from water/acetone.

The new compounds of formula I and salts thereof according to the invention can be administered enterally or parenterally in a liquid or solid form. In this connection all the usual forms of administration come into consideration such as tablets, capsules, coated tablets, syrups, solutions, suspension, etc. Water which contains additives such as stabilizers, solubilizers and buffers that are usual in injection solutions is preferably used as the injection medium.

Such additives may be tartrate and citrate buffer, ethanol, complexing agents (such as ethylenediaminetetraacetic acid and non-toxic salts thereof), high-molecular polymers (such as liquid polyethylene glycols) to regulate viscosity. Liquid carrier substances for injection solutions must be sterile and are preferably dispensed into ampoules. Solid carrier substances include starch, lactose, mannitol, methylcellulose, talcum, highly dispersed silicic acids, higher molecular fatty acids (such as stearic acid), gelatins, agar-agar, calcium phosphate, magnesium stearate, animal and vegetable fats, solid high-molecular polymers (such as polyethylene glycols); and suitable preparations for oral application can optionally also contain flavorings and sweeteners.

The dosage depends on various factors such as manner of administration, species, age and/or individual state of health. The doses to be administered daily are about 5–400 mg/kg, preferably about 10–100 mg/kg, and can be taken singly or distributed over several administrations.

The invention is further illustrated by the following, non-limiting examples.

EXAMPLE 1

The compounds listed in Table 1 have been prepared according to the following general procedure:

The carboxylic acid (appr. 20 mg, 1.2 equivalents) was dissolved in a 0.2 M solution of diisopropylamine in dimethylformamide corresponding to 3.6 equivalents of base. To the stirring solution was added a 0.1 M solution of O-benzotriazol-1-yl-N,N,N',N'-tetramethyluronium tetrafluoroborate (TBTU) in DMF corresponding to 1.20 equivalents, followed after 60 min by a 0.1 M solution of the diamine Aryl($NH_2$)$_2$ in DMF corresponding to 1 equivalent. The mixture was stirred overnight. The product was isolated by method A or method B below.

Method A: Acidic Ion Exchange Column

The crude reaction mixture was loaded onto an acidic ion-exchange column (45 mm, 15 mm ID) charged with Fractogel EMD $SO_3$-650 (S) previously conditioned with 1 molar sulphuric acid in methanol/water (9:1.) and washed with methanol/water 9:1. The column was rinsed with water followed by methanol. The product was then eluted with 0.4 M pyridine in methanol followed by 0.2 M ammonia in methanol. The product fractions were identified by LC/MS, combined and evaporated.

Method B: Reversed-phase Column

The crude reaction mixture was evaporated, the residue dissolved in methanol and loaded onto a reversed-phase column (Kromasil C18,10 μm, 250 mm, 20 mm ID). The column was eluted with a gradient of methanol in water (50% methanol/water—100% methanol). The product fractions were identified by LC/MS, combined and evaporated. Product identity and purity were confirmed by mass spectrometry (atmosperic pressure ionization) and HPLC equipped with mass detection (LC/MS).

TABLE 1

| Compound Number | Molecule Name | Work-up procedure | MW found [M + H] | Exact MW [M + H] calc'd |
|---|---|---|---|---|
| 1 | Benzofuran-2-carboxylic acid (2-amino-phenyl)-amide | A | 253.3 | 253.10 |
| 2 | Furan-2-carboxylic acid (2-amino-phenyl)-amide | A | 203.3 | 203.08 |
| 3 | 1-Methyl-1H-pyrrole-2-carboxylic acid (2-amino-phenyl)-amide | A | 216.2 | 216.11 |
| 4 | 3,5-Dimethyl-isoxazole-4-carboxylic acid (2-amino-phenyl)-amide | A | 232.3 | 232.11 |
| 5 | 5-Oxo-pyrrolidine-2-carboxylic acid (2-amino-phenyl)-amide | A | 220.3 | 220.11 |
| 6 | 1H-Pyrrole-2-carboxylic acid (2-amino-phenyl)-amide | A | 202.3 | 202.10 |
| 7 | 5-Methyl-3-phenyl-isoxazole-4-carboxylic acid (2-amino-phenyl)-amide | A | 294.3 | 294.12 |
| 8 | 5-Phenethyl-4,5-dihydro-isoxazole-3-carboxylic acid (2-amino-phenyl)-amide | A | 310.4 | 310.16 |
| 9 | 5,6-Dimethoxy-benzo[b]thiophene-2-carboxylic acid (2-amino-phenyl)-amide | A | 329.5 | 329.10 |
| 10 | 3-Methyl-isoxazole-5-carboxylic acid (2-amino-phenyl)-amide | A | 218.3 | 218.09 |
| 11 | 2,5-Dimethyl-2H-pyrazole-3-carboxylic acid (2-amino-phenyl)-amide | A | 231.3 | 231.12 |
| 12 | 1,5-Dimethyl-1H-pyrazole-3-carboxylic acid (2-amino-phenyl)-amide | A | 231.3 | 231.12 |
| 13 | 5-Propoxy-1H-indole-2-carboxylic acid (2-amino-phenyl)-amide | A | 310.4 | 310.16 |
| 14 | 5-Allyloxy-1H-indole-2-carboxylic acid (2-amino-phenyl)-amide | A | 308.5 | 308.14 |
| 15 | 3H-Benzo[e]indole-2-carboxylic acid (2-amino-phenyl)-amide | A | 302.5 | 302.13 |
| 16 | 5-Methyl-2H-pyrazole-3-carboxylic acid (2-amino-phenyl)-amide | A | 217.3 | 217.11 |

TABLE 1-continued

| Compound Number | Molecule Name | Work-up procedure | MW found [M + H] | Exact MW [M + H] calc'd |
|---|---|---|---|---|
| 17 | 3-Phenyl-1H-indole-2-carboxylic acid (2-amino-phenyl)-amide | A | 328.4 | 328.15 |
| 18 | 3-Methyl-5-phenyl-isoxazole-4-carboxylic acid (2-amino-phenyl)-amide | A | 294.3 | 294.12 |
| 19 | 1-Acetyl-piperidine-4-carboxylic acid (2-amino-phenyl)-amide | A | 262.4 | 262.16 |
| 20 | Cyclohex-1-enecarboxylic acid (2-amino-phenyl)-amide | A | 217.3 | 217.13 |
| 21 | 3-(2-Methoxy-ethoxy)-thiophene-2-carboxylic acid (2-amino-phenyl)-amide | A | 293.4 | 293.10 |
| 22 | 1,5-Dimethyl-3-oxo-2-penyl-2,3-dihydro-1H-pyrazole-4-carboxylic acid (2-amino-phenyl)-amide | A | 323.5 | 323.15 |
| 23 | 7-Methoxy-benzofuran-2-carboxylic acid (2-amino-phenyl)-amide | A | 283.3 | 283.11 |
| 24 | 1H-Imidazole-2-carboxylic acid (2-amino-phenyl)-amide | A | 203.3 | 203.09 |
| 25 | 5-(4-Chloro-phenyl)-1H-pyrazole-3-carboxylic acid (2-amino-phenyl)-amide | A | 313.3 | 313.09 |
| 26 | 7-Methoxy-benzo[b]thiophene-2-carboxylic acid (2-amino-phenyl)-amide | A | 299.4 | 299.09 |
| 27 | 2-Phenyl-2H-[1,2,3]triazole-4-carboxylic acid (2-amino-phenyl)-amide | A | 280.3 | 280.12 |
| 28 | 2-Chloro-thiazole-4-carboxylic acid (2-amino-phenyl)-amide | A | 254.3 | 254.02 |
| 29 | 2-Benzyl-5-methyl-2H-pyrazole-3-carboxylic acid (2-amino-phenyl)-amide | A | 307.4 | 307.16 |
| 30 | 5-Methyl-1-phenyl-1H-pyrazole-3-carboxylic acid (2-amino-phenyl)-amide | A | 293.5 | 293.14 |
| 31 | 5-Methyl-1-phenyl-1H-[1,2,3]triazole-4-carboxylic acid (2-amino-phenyl)-amide | A | 294.3 | 294.14 |
| 32 | 5-Methyl-2-phenyl-oxazole-4-carboxylic acid (2-amino-phenyl)-amide | A | 294.3 | 294.12 |
| 33 | 2,5-Dimethyl-4-nitro-2H-pyrazole-3-carboxylic acid (2-amino-phenyl)-amide | A | 276.3 | 276.11 |
| 34 | 1H-Indole-2-carboxylic acid (2-amino-phenyl)-amide | A | 252.3 | 252.11 |
| 35 | 4-Acetyl-3,5-dimethyl-1H-pyrrole-2-carboxylic acid (2-amino-phenyl)-amide | A | 272.4 | 272.14 |
| 36 | 6-Oxo-1,4,5,6-tetrahydro-pyridazine-3-carboxylic acid (2-amino-phenyl)-amide | A | 233.4 | 233.10 |
| 37 | 5-Phenyl-isoxazole-3-carboxylic acid (2-amino-phenyl)-amide | A | 280.3 | 280.11 |
| 38 | Thiazole-4-carboxylic acid (2-amino-phenyl)-amide | A | 220.2 | 220.05 |
| 39 | Benzofuran-2-carboxylic acid (2-amino-4,5-dichloro-phenyl)-amide | B | 321.2 | 321.02 |
| 40 | Furan-2-carboxylic acid (2-amino-4,5-dichloro-phenyl)-amide | B | 271.2 | 271.00 |
| 41 | 3,5-Dimethyl-isoxazole-4-carboxylic acid (2-amino-4,5-dichloro-phenyl)-amide | B | 300.2 | 300.03 |
| 42 | 5-Oxo-pyrrolidine-2-carboxylic acid (2-amino-4,5-dichloro-phenyl)-amide | B | 288.2 | 288.03 |
| 43 | 5-Methyl-3-phenyl-isoxazole-4-carboxylic acid (2-amino-4,5-dichloro-phenyl)-amide | B | 362.4 | 362.05 |
| 44 | 5,6-Dimethoxy-benzo[b]thiophene-2-carboxylic acid (2-amino-4,5-dichloro-phenyl)-amide | B | 397.3 | 397.02 |
| 45 | 2,5-Dimethyl-2H-pyrazole-3-carboxylic acid (2-amino-4,5-dichloro-phenyl)-amide | B | 299.4 | 299.05 |
| 46 | 1,5-Dimethyl-1H-pyrazole-3-carboxylic acid (2-amino-4,5-dichloro-phenyl)-amide | B | 299.4 | 299.05 |
| 47 | 5-Propoxy-1H-indole-2-carboxylic acid (2-amino-4,5-dichloro-phenyl)-amide | B | 378.3 | 378.08 |
| 48 | 5-Allyloxy-1H-indole-2-carboxylic acid (2-amino-4,5-dichloro-phenyl)-amide | B | 376.4 | 376.06 |
| 49 | 3H-Benzo[e]indole-2-carboxylic acid (2-amino-4,5-dichloro-phenyl)-amide | B | 370.3 | 370.05 |
| 50 | 5-Methyl-2H-pyrazole-3-carboxylic acid (2-amino-4,5-dichloro-phenyl)-amide | B | 285.2 | 285.03 |
| 51 | 1-Acetyl-piperidine-4-carboxylic acid (2-amino-4,5-dichloro-phenyl)-amide | B | 330.3 | 330.08 |
| 52 | Cyclohex-1-enecarboxylic acid (2-amino-4,5-dichloro-phenyl)-amide | B | 285.2 | 285.06 |

TABLE 1-continued

| Compound Number | Molecule Name | Work-up procedure | MW found [M + H] | Exact MW [M + H] calc'd |
|---|---|---|---|---|
| 53 | 3-(2-Methoxy-ethoxy)-thiophene-2-carboxylic acid (2-amino-4,5-dichloro-phenyl)-amide | B | 361.3 | 361.02 |
| 54 | 1,5-Dimethyl-3-oxo-2-phenyl-2,3-dihydro-1H-pyrazole-4-carboxylic acid (2-amino-4,5-dichloro-phenyl)-amide | B | 391.4 | 391.07 |
| 55 | 7-Methoxy-benzofuran-2-carboxylic acid (2-amino-4,5-dichloro-phenyl)-amide | B | 351.2 | 351.03 |
| 56 | 7-Methoxy-benzo[b]thiophene-2-carboxylic acid (2-amino-4,5-dichloro-phenyl)-amide | B | 367.3 | 367.01 |
| 57 | 2-Phenyl-2H-[1,2,3]triazole-4-carboxylic acid (2-amino-4,5-dichloro-phenyl)-amide | B | 348.3 | 348.04 |
| 58 | 5-Phenyl-thiazole-4-carboxylic acid (2-amino-4,5-dichloro-phenyl)-amide | B | 364.3 | 364.01 |
| 59 | 2-Chloro-thiazole-4-carboxylic acid (2-amino-4,5-dichloro-phenyl)-amide | B | 322.1 | 321.94 |
| 60 | 2-Benzyl-5-methyl-2H-pyrazole-3-carboxylic acid (2-amino-4,5-dichloro-phenyl)-amide | B | 375.3 | 375.08 |
| 61 | 5-Methyl-1-phenyl-1H-pyrazole-3-carboxylic acid (2-amino-4,5-dichloro-phenyl)-amide | B | 361.4 | 361.06 |
| 62 | 5-Methyl-1-phenyl-1H-[1,2,3]triazole-4-carboxylic acid (2-amino-4,5-dichloro-phenyl)-amide | B | 362.5 | 362.06 |
| 63 | 5-Methyl-2-phenyl-oxazole-4-carboxylic acid (2-amino-4,5-dichloro-phenyl)-amide | B | 362.4 | 362.05 |
| 64 | 1H-Indole-2-carboxylic acid (2-amino-4,5-dichloro-phenyl)-amide | B | 320.4 | 320.04 |
| 65 | 4-Acetyl-3,5-dimethyl-1H-pyrrole-2-carboxylic acid (2-amino-4,5-dichloro-phenyl)-amide | B | 340.3 | 340.06 |
| 66 | 6-Oxo-1,4,5,6-tetrahydro-pyridazine-3-carboxylic acid (2-amino-4,5-dichloro-phenyl)-amide | B | 301.3 | 301.03 |
| 67 | Thiazole-4-carboxylic acid (2-amino-4,5-dichloro-phenyl)-amide | B | 288.3 | 287.98 |
| 68 | Benzofuran-2-carboxylic acid (2-amino-pyridin-3-yl)-amide | B | 254.4 | 254.09 |
| 69 | 5-Phenethyl-4,5-dihydro-isoxazole-3-carboxylic acid (2-amino-pyridin-3-yl)-amide | B | 311.5 | 311.15 |
| 70 | 5-Allyloxy-1H-indole-2-carboxylic acid (2-amino-pyridin-3-yl)-amide | B | 309.3 | 309.14 |
| 71 | Cyclohex-1-enecarboxylic acid (2-amino-pyridin-3-yl)-amide | B | 218.4 | 218.13 |
| 72 | 1,5-Dimethyl-3-oxo-2-phenyl-2,3-dihydro-1H-pyrazole-4-carboxylic acid (2-amino-pyridin-3-yl)-amide | B | 324.3 | 324.15 |
| 73 | 7-Methoxy-benzofuran-2-carboxylic acid (2-amino-pyridin-3-yl)-amide | B | 284.4 | 284.10 |
| 74 | 7-Methoxy-benzo[b]thiophene-2-carboxylic acid (2-amino-pyridin-3-yl)-amide | B | 300.3 | 300.08 |
| 75 | 2-Phenyl-2H-[1,2,3]triazole-4-carboxylic acid (2-amino-pyridin-3-yl)-amide | B | 281.4 | 281.12 |
| 76 | 5-Phenyl-thiazole-4-carboxylic acid (2-amino-pyridin-3-yl)-amide | B | 297.3 | 297.08 |
| 77 | 2-Benzyl-5-methyl-2H-pyrazole-3-carboxylic acid (2-amino-pyridin-3-yl)-amide | B | 308.5 | 308.15 |
| 78 | 5-Methyl-1-phenyl-1H-[1,2,3]triazole-4-carboxylic acid (2-amino-pyridin-3-yl)-amide | B | 295.4 | 295.13 |
| 79 | 5-Methyl-2-phenyl-oxazole-4-carboxylic acid (2-amino-pyridin-3-yl)-amide | B | 295.4 | 295.12 |
| 80 | 2,5-Dimethyl-4-nitro-2H-pyrazole-3-carboxylic acid (2-amino-pyridin-3-yl)-amide | B | 277.3 | 277.11 |
| 81 | Benzofuran-2-carboxylic acid (4-amino-pyrimidin-5-yl)-amide | B | 255.2 | 255.09 |
| 82 | 5-Phenethyl-4,5-dihydro-isoxazole-3-carboxylic acid (4-amino-pyrimidin-5-yl)-amide | B | 312.3 | 312.15 |
| 83 | Cyclohex-1-enecarboxylic acid (4-amino-pyrimidin-5-yl)-amide | B | 219.3 | 219.12 |
| 84 | 3-(2-Methoxy-ethoxy)-thiophene-2-carboxylic acid (4-amino-pyrimidin-5-yl)-amide | B | 295.3 | 295.09 |
| 85 | 1,5-Dimethyl-3-oxo-2-phenyl-2,3-dihydro-1H-pyrazole-4-carboxylic acid (4-amino-pyrimidin-5-yl)-amide | B | 325.4 | 325.14 |
| 86 | 7-Methoxy-benzofuran-2-carboxylic acid (4- | B | 285.3 | 285.10 |

TABLE 1-continued

| Compound Number | Molecule Name | Work-up procedure | MW found [M + H] | Exact MW [M + H] calc'd |
|---|---|---|---|---|
| | amino-pyrimidin-5-yl)-amide | | | |
| 87 | 7-Methoxy-benzo[b]thiophene-2-carboxylic acid (4-amino-pyrimidin-5-yl)-amide | B | 301.3 | 301.08 |
| 88 | 2-Phenyl-2H-[1,2,3]triazole-4-carboxylic acid (4-amino-pyrimidin-5-yl)-amide | B | 282.3 | 282.11 |
| 89 | 5-Phenyl-thiazole-4-carboxylic acid (4-amino-pyrimidin-5-yl)-amide | B | 298.3 | 298.08 |
| 90 | 2-Benzyl-5-methyl-2H-pyrazole-3-carboxylic acid (4-amino-pyrimidin-5-yl)-amide | B | 309.3 | 309.15 |
| 91 | 5-Methyl-1-phenyl-1H-[1,2,3]triazole-4-carboxylic acid (4-amino-pyrimidin-5-yl)-amid | B | 296.5 | 296.13 |
| 92 | 5-Methyl-2-phenyl-oxazole-4-carboxylic acid (4-amino-pyrimidin-5-yl)-amide | B | 296.4 | 296.11 |
| 93 | 5-methoxy-benzofuran-2-carboxylic acid (2-amino-phenyl)-amide | A | 283.0 | 283.11 |
| 94 | 6,7-dimethyl-benzofuran-2-carboxylic acid (2-amino-phenyl)-amide | A | 281.0 | 281.13 |
| 95 | 5-nitro-benzofuran-2-carboxylic acid (2-amino-phenyl)-amide | A | 298.0 | 298.08 |
| 96 | 6-methoxy-benzofuran-2-carboxylic acid (2-amino-phenyl)-amide | A | 283.2 | 283.11 |
| 97 | 6-methoxy-1H-indole-2-carboxylic acid (2-amino-phenyl)-amide | A | 282.2 | 282.12 |
| 98 | 4-chloro-5-methoxy-1H-indole-2-carboxylic acid (2-amino-phenyl)-amide | A | 316.2 | 316.09 |
| 99 | 3-methoxy-5-methyl-1H-indole-2-carboxylic acid (2-amino-phenyl)-amide | A | 296.2 | 296.14 |
| 100 | 3-pyrrol-1-yl-1H-indole-2-carboxylic acid (2-amino-phenyl)-amide | A | 317.2 | 317.14 |
| 101 | 7-nitro-1H-indole-2-carboxylic acid (2-amino-phenyl)-amide | A | 297.1 | 297.10 |
| 102 | 5,7-dimethoxy-1H-indole-2-carboxylic acid (2-amino-phenyl)-amide | A | 312.2 | 312.13 |
| 103 | 5-Methoxy-1H-indole-2-carboxylic acid (2-amino-phenyl)-amide | A | 282.2 | 282.12 |
| 104 | 6-Methoxy-4-trifluoromethyl-1H-indole-2-carboxylic acid (2-amino-phenyl)-amide | A | 350.2 | 350.11 |
| 105 | 5-Methoxy-1-methyl-3-methylsulfanyl-1H-indole-2-carboxylic acid (2-amino-phenyl)-amide | A | 342.3 | 342.13 |

EXAMPLE 2

In order to investigate the differentiation-inducing effect of the compounds and compositions according to this invention, two assays were used.

A) Assay for Inhibition of Histone Deacetylase (HDAC)

Principle:

HDAC deacetylates lysines in histone H4. A 17 aa peptide with TAMRA at the C-terminus and QSY7 at the N-terminus was used as a substrate. Following deacetylation by HDAC the enzyme Lys C is able to cleave the peptide resulting in disappearence of the quench effect and a high signal. Inhibition of HDAC by compounds results in low signals because Lys C has no substrate for cleaving and the quench effect persists.

Assay:

For dose response curves 10 concentrations were diluted starting at 30 uM. 10 ul compound dilution were put into each well of a 384 well plate. 10 ul HDAC (rec. HDAC-1 purified from HEK 293 cells; activity was assessed for each preparation) were added. 10 ul peptide was added (1 uM final concentration). After 90 min incubation at room temperature the reaction was stopped by addition of 20 ul test buffer including 3 ug/ml Lys C and 0.075% SDS. After overnight incubation the fluorescent signal of TAMRA was measured at absorption 544 nm, emission 590 nm by Victor 2.

B) E-cadherin Upregulation Assay

Assay Principle

E-cadherin as an adhesion molecule is important for connection of the cells and integrity of tissues. There are tumor cells where E-cadherin protein is downregulated allowing cells to metastasize. Upregulation of the protein in cells where there is insufficient E-cadherin is regarded as a marker for the differentiation of the tumor cell. This corresponds to leaving the undifferentiated tumor cell status.

The compounds described are able to upregulate expression of E-cadherin in A549. In parallel, the proliferation of the cells is examined. The activity of an E-cadherin upregulator is defined as an increase in E-cadherin expression determined by an ELISA. Cell proliferation is also determined by WST-1 in the same well.

Method

The assay was performed in 384-well format. A549 (ATCC: CCL-185), a human lung carcinoma cell line, showed very low expression of E-cadherin. 5000 cells per well were seeded in culture medium with 10% FCS at day 1. At day 2 compounds in different concentrations starting at 40 uM were added at a final concentration of DMSO of 0.5%. At day 4, WST-1 reagent was added and absorption was measured after 45 min (450 nm/690 nm).

The medium was aspirated, 100 ul fixation solution was added per well and discarded after 30 min, followed by addition of 100 ul blocking solution. Addition of 20 µl/well mAb anti-E-cad (clone 6F9), final conc. 0,3 µg/ml for 60 min. Three washing steps with PBS/Tween 100 µl/well. Addition of mAb anti-mouse-Ig-Biotin (20 µl/well) was performed for 60 min. Three washing steps were performed with PBS/Tween. Addition of Streptavidin-POD (20 µl/well) was performed for 60 min. Three washing steps were performed with PBS/Tween. Addition of 50 µl ABTS substrate was performed for 5 min and finally addition of 12.5 ul oxalic acid to stop the reaction. Absorption was measured at 405 nm.

Calculation of EC50:

% proliferation of cells is substracted from % E-cadherin expression resulting in Delta. The dose response curve resulting from 10 concentrations was calculated using XLfit. EC50 is the concentration where 50% of cells show real upregulation of E-cadherin protein expression.

TABLE 2

| Compound No. | E-cadherin upregulation EC50 [µM] (Assay B) | HDAC IC50 [uM] (Assay A) |
|---|---|---|
| 38 | 5.9 | 11.05 |

EXAMPLE 3

Tablet Formulation (Wet Granulation):

| Item | Ingredients | mg/tablet | | | |
|---|---|---|---|---|---|
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation:

| Item | Ingredients | Mg/capsule | | | |
|---|---|---|---|---|---|
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

1. Manufacturing Procedure:
2. Mix items 1, 2 and 3 in a suitable mixer for 30 minutes.
3. Add items 4 and 5 and mix for 3 minutes.
4. Fill into a suitable capsule.

EXAMPLE 4

Pharmacological Test Report
Method

Female Balb/C nu/nu-mice(n=12 per group), aged 8–10 weeks, were subcutaneously injected with 5*106 SW620 colon carcinoma cells. On day 6, animals with tumor volumes of about 200 mm³ were randomly assigned to treatment groups. The test compound was administered as a fine suspension in 0.5% methylcellulose with an application volume of 10 ml/kg based on actual body weights. Oral treatment started on day 8 and continued through to day 27 on a once daily, 7 times per week treatment schedule.

Results

Effect on tumor volumes at the end of the study:

TABLE 3

| | Tumor volume (mm³) | % inhibition vs. control |
|---|---|---|
| Vehicle | 2200.0 | 0 |
| Compound No. 38 | 1029.0 | 53 |

The volume of the tumor was determined from the following equation:

Volume of a tumor=½×(major axis)×(minor axis)2

What is claimed is:

1. A compound selected from the group consisting of:
   3,5-Dimethyl-isoxazole-4-carboxylic acid (2-amino-4,5-dichloro-phenyl)-amide;
   5-Oxo-pyrrolidine-2-carboxylic acid (2-amino-4,5-dichloro-phenyl)-amide;
   5-Methyl-3-phenyl-isoxazole-4-carboxylic acid (2-amino-4,5-dichloro-phenyl)-amide;
   5,6-Dimethoxy-benzo[b]thiophene-2-carboxylic acid (2-amino-4,5-dichloro-phenyl)-amide;
   2,5-Dimethyl-2H-pyrazole-3-carboxylic acid (2-amino-4,5-dichloro-phenyl)-amide;
   1,5-Dimethyl-1H-pyrazole-3-carboxylic acid (2-amino-4,5-dichloro-phenyl)-amide;
   5-Propoxy-1H-indole-2-carboxylic acid (2-amino-4,5-dichloro-phenyl)-amide;
   5-Allyloxy-1H-indole-2-carboxylic acid (2-amino-4,5-dichloro-phenyl)-amide;
   3H-Benzo[e]indole-2-carboxylic acid (2-amino-4,5-dichloro-phenyl)-amide;
   5-Methyl-2H-pyrazole-3-carboxylic acid (2-amino-4,5-dichloro-phenyl)-amide; and
   pharmaceutically acceptable salts of any of the foregoing.

2. A compound selected from the group consisting of:
   1-Acetyl-piperidine-4-carboxylic acid (2-amino-4,5-dichloro-phenyl)-amide;
   Cyclohex-1-enecarboxylic acid (2-amino-4,5-dichloro-phenyl)-amide;
   3-(2-Methoxy-ethoxy)-thiophene-2-carboxylic acid (2-amino-4,5-dichloro-phenyl)-amide;
   1,5-Dimethyl-3-oxo-2-phenyl-2 3-dihydro-1H-pyrazole-4-carboxylic acid (2-amino-4,5-dichloro-phenyl)-amide;
   7-Methoxy-benzofuran-2-carboxylic acid (2-amino-4,5-dichloro-phenyl)-amide;
   7-Methoxy-benzo[b]thiophene-2-carboxylic acid (2-amino-4,5-dichloro-phenyl)-amide;
   2-Phenyl-2H-[1,2,3]triazole-4-carboxylic acid (2-amino-4,5-dichloro-phenyl)-amide;
   5-Phenyl-thiazole-4-carboxylic acid (2-amino-4,5-dichloro-phenyl)-amide;
   2-Chloro-thiazole-4-carboxylic acid (2-amino-4,5-dichloro-phenyl)-amide;
   2-Benzyl-5-methyl-2H-pyrazole-3-carboxylic acid (2-amino-4,5-dichloro-phenyl)-amide;

and pharmaceutically acceptable salts of any of the foregoing.

3. A compound selected from the group consisting of:

5-Methyl-1-phenyl-1H-pyrazole-3-carboxylic acid (2-amino-4,5-dichloro-phenyl)-amide;

5-Methyl-1-phenyl-1H-[1,2,3]triazole-4-carboxylic acid (2-amino-4,5-dichloro-phenyl)-amide;

5-Methyl-2-phenyl-oxazole-4-carboxylic acid (2-amino-4,5-dichloro-phenyl)-amide;

1H-Indole-2-carboxylic acid (2-amino-4,5-dichloro-phenyl)-amide;

4-Acetyl-3,5-dimethyl-1H-pyrrole-2-carboxylic acid (2-amino-4,5-dichloro-phenyl)-amide;

6-Oxo-1,4,5,6-tetrahydro-pyridazine-3-carboxylic acid (2-amino-4,5-dichloro-phenyl)-amide;

Thiazole-4-carboxylic acid (2-amino-4,5-dichloro-phenyl)-amide; and pharmaceutically acceptable salts of any of the foregoing.

4. A pharmaceutical composition comprising a compound of claim 1 and a pharmaceutically acceptable excipient or diluent.

5. A pharmaceutical composition comprising a compound of claim 2 and a pharmaceutically acceptable excipient or diluent.

6. A pharmaceutical composition comprising a compound of claim 3 and a pharmaceutically acceptable excipient or diluent.

7. A method of treating colon cancer or leukemia, comprising administering, to a patient in need thereof, a therapeutically effective amount of a compound of claim 1.

8. A method of treating colon cancer or leukemia, comprising administering, to a patient in need thereof, a therapeutically effective amount of a compound of claim 2.

9. A method of treating colon cancer or leukemia, comprising administering, to a patient in need thereof, a therapeutically effective amount of a compound of claim 3.

* * * * *